(12) United States Patent
Chmielewski et al.

(10) Patent No.: US 9,376,460 B2
(45) Date of Patent: Jun. 28, 2016

(54) METHOD OF POLYPHOSPHATE SYNTHESIS

(71) Applicant: INSTYTUT CHEMII BIOORGANICZNEJ POLSKIEJ AKADEMII NAUK, Poznań (PL)

(72) Inventors: Marcin Krzysztof Chmielewski, Poznań (PL); Joanna Romanowska, Luboń (PL)

(73) Assignee: INSTYTUT CHEMII BIOORGANICZNEJ POLSKIEJ AKADEMII NAUK, Poznan (PL)

( * ) Notice: Subject to any disclaimer, the term of this patent is extended or adjusted under 35 U.S.C. 154(b) by 0 days.

(21) Appl. No.: 14/412,951

(22) PCT Filed: Jul. 29, 2013

(86) PCT No.: PCT/PL2013/000098
§ 371 (c)(1),
(2) Date: Jan. 5, 2015

(87) PCT Pub. No.: WO2014/025272
PCT Pub. Date: Feb. 13, 2014

(65) Prior Publication Data
US 2015/0203524 A1    Jul. 23, 2015

(30) Foreign Application Priority Data
Aug. 5, 2012 (PL) ......................... 400248

(51) Int. Cl.
C07H 21/00 (2006.01)
C07H 19/10 (2006.01)
C07H 1/04 (2006.01)
C07F 9/6584 (2006.01)
C07H 1/02 (2006.01)

(52) U.S. Cl.
CPC ............ *C07H 19/10* (2013.01); *C07F 9/65844* (2013.01); *C07H 1/04* (2013.01); *C07H 1/02* (2013.01)

(58) Field of Classification Search
None
See application file for complete search history.

(56) References Cited

PUBLICATIONS

Chmielewski Organic Letters (2009), vol. 11, pp. 3742-3745.*
Sun et al. Organic Letters (2008), vol. 10, pp. 1703-1706.*
Ludwig, J., "A New Route to Nucleoside 5'-triphosphates," Acta Biochimica et Biophisica Academiae Scientiarum Hungaricae, vol. 16, No. 3-4, pp. 131-133, (1981).
Ruth, Jerry L. et al., "Nucleoside Analogues with Clinical Potential in Antivirus Chemotherapy: The Effect of Several Thymidine and 2'-Deoxycytidine Analogue 5'-Triphosphates on Purified Human (a, B) and Herpes Simplex Virus (Types 1, 2) DNA Polymerases," Molecular Pharmacology, vol. 20, pp. 415-422 (1981).
Wu, Weidong et al., "A Combination Chemical and Enzymatic Approach for the Preparation of Azole Carboxamide Nucleoside Triphosphate," Journal of Organic Chemistry, (2003), vol. 68, pp. 3860-3865.
Gillerman, Irina et al., "An Improved One-Pot Synthesis of Nucleoside 5'-Triphosphate Analogues," Nucleosides, Nucleotides and Nucleic Acids, vol. 29, pp. 245-256 (2010).
Tomasz, J. et al., "Chemical Synthesis of 5'pyrophosphate and triphosphate derivatives of 3'-5' ApA, ApG, GpA and GpG," Nucleic Acids Research, vol. 5, No. 8, Aug. 1978, pp. 2945-2957.
Simoncsits, A. et al., "Necleoside 5'-phosphordiamidates, sythesis and Some Properties," Nucleic Acids Research, vol. 2, No. 7, Jul. 1975, pp. 1223-1233.
Moffat, J.G. et al., "Nucleoside Polyphophates. X. The Synthesis and Some Reactions of Nucleoside-5' Phosphoromorpholidates and Related Compounds. Imporved Methods for the Preparation of Nucleoside-5' Polyphosphates," Nucleoside-5' Phosphoromopholidates, Feb. 5, 1961, vol. 83, pp. 649-658.
Moffat, J.G., "A General Synthesis of Nucleoside-5' Triphosphates," Syntex Institute for Molecular Biology, vol. 42, (1964), pp. 599-604.
Van Boom, J.H. et al., "2,2,2-Tribromoethyl Phosphoromorpholinochloridate: A Convenient Reagent for the Synthesis of Ribonucleoside Mono-, Di- and Tri-Phosphates," Tetrahedron Letters, No. 32, pp. 2779-2782 (1975).
Hoard, Donald E. et al., "Conversion of Mono- and Oligodeoxyribonucleotides to 5'-Triphosphates," Journal of the American Chemical Society, vol. 87, No. 8, Apr. 20, 1965, pp. 1785-1788.
Shimazu, Masamitsu et al., "Facile Synthesis of nucleotides Containing Polyphosphates by Mn(II) and Cd(II) Ion-Catalyzed Pyrophasphate Bond Formation in Aqueous Solution," Tetrahedron Letters, vol. 31, No. 2, pp. 235-238, (1990).
Wu, Weidong et al., "A Novel Method for the Preparation of Nucleoside Triphosphates from Activated Nucleoside Phosphoramidates," Organic Letters, vol. 6, No. 13, pp. 2257-2260, (2004).
Ludwig, János et al., "Rapid and Efficient Synthesis of Nucleoside 5'-O-(1-Thiotriphosphates), 5'-Tri[phosphates and 2',3'-Cyclophosphorothioates using 2-Chloro-4H-1,3,2-benzodioxaphosphorin-4-one," Journal of Organic Chemistry, vol. 54, pp. 631-635, (1989).

(Continued)

Primary Examiner — Patrick Lewis
(74) Attorney, Agent, or Firm — Oliff PLC

(57) ABSTRACT

The subject of the invention is a new method of the synthesis of polyphosphate analogs, such as nucleosides, oligonucleotides, carbohydrates, peptides and proteins, which are of biological importance and are used in organic chemistry, molecular biology and biotechnology. Polyphosphate analogs, including in particular nucleoside 5'-triphosphates, display high biological activity and are responsible for the provision and storage of energy in live organisms. The method relates to the synthesis of organic polyphosphates of general formula (1), where n has a value of 0 to 2, while X stands for an organic radical, in particular nucleoside, oligonucleotide, peptide-carbohydrate or a protein radical.

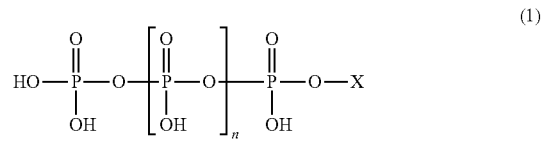

(1)

22 Claims, No Drawings

(56) References Cited

PUBLICATIONS

Warnecke, Svenja et al., "Synthesis of Nucleoside Di- and Tri-phosphates and Dinucleoside Polyphosphates with cycloSal-Nucleotides," Journal of Organic Chemistry, vol. 74, pp. 3024-3030, (2009).

Chimielewski, Marcin K., "Protecting of a Thermolabile Protecting Group: 'Click-Clack' Approach," Organic Letters, vol. 11, No. 16, pp. 3742-3745, (2009).

Ratajczak, Tomasz et al., "Oxidation of H-Phosphates with Iodine by Intramolecular Support of a 2-Pyridyl Thermolabile Protecting Group," Journal of Organic Chemistry, vol. 77, pp. 7866-7872, (2012).

Oct. 22, 2013 International Search Report issued in International Patent Application No. PCT/PL2013/000098.

Oct. 22, 2013 International Written Opinion issued in International Patent Application No. PCT/PL2013/000098.

* cited by examiner

METHOD OF POLYPHOSPHATE SYNTHESIS

The subject of the invention is a new method of the synthesis of polyphosphate analogues, such as nucleosides, oligonucleotides, carbohydrates, peptides and proteins, which are of biological importance and are used in organic chemistry, molecular biology and biotechnology. Polyphosphate analogues, including in particular nucleoside 5'-triphosphates, display high biological activity and are responsible for the provision and storage of energy in live organisms. Moreover, nucleoside 5'-triphosphates serve as basic units in the enzymatic synthesis of DNA molecules in live organisms' cells and are widely used in both basic research and advanced diagnostic and therapeutic processes. Due to their properties, as well as the fact that they serve as substrates for polymerases, nucleoside 5'-triphosphates are used in many biological applications catalyzed by the enzymes. Nucleoside 5'-triphosphates are mostly used as substrates in polymerase chain reactions to multiply DNA matrix with the use of polymerase.

Due to the application potential of triphosphate nucleoside analogues and oligonucleotides, there is a great interest in new efficient methods of obtaining the compound. Nowadays, nucleoside 5'-triphosphates are most frequently obtained by means of biological methods, in which native DNA is degraded. At the same time, many synthetic studies are being conducted with the aim of designing new methods of obtaining triphosphate analogues through chemical synthesis. Such methods would make it possible to expand the scale of the synthesis, maintaining the high quality and purity of the end product.

The available literature describes methods of the chemical synthesis of nucleoside 5'-triphosphates based on the reaction of properly activated nucleoside monophosphate with pyrophosphate. In the most frequently used chemical method, nucleoside dichlorophosphate is generated in a reaction with bis(tri-n-butylamine) pyrophosphate, followed by the hydrolysis of the achieved cyclical intermediate product, which was discussed by: Ludwig, J. Acta Biochim. Biophys. Acad. Sci. Hung. 1981, 16, 131-3, Ruth, J. L.; Cheng, Y. C. Mol. Pharmacol. 1981, 20, 415-22. However, this method is not universal, as it cannot be used in the synthesis of nucleotide triphosphates modified in heterocyclic bases, as described by Wu, W.; Bergstrom, D. E.; Davisson, V. J. J. Org. Chem. 2003, 68, 3860-5, and due to the by-products of the reaction, which was described by Gillerman, J.; Fischer, B., Nucleosides, Nucleotides & Nucleic Acids, 2010, 29, 245-256.

Another method of nucleoside 5'-triphosphate synthesis described in literature is based on a reaction of the activated nucleoside monophosphate in the form of the non-substituted phosphoroamidate, as presented by Tomasz, J.; Simoncsits, A.; Kajtar, M.; Krug, R. M.; Shatkin, A., J. Nucleic Acids Res. 1978, 5, 2945-57 and Simoncsits, A.; Tomasz, J. Nucleic Acids Res. 1975, 2, 1223-33), or N-morpholine phosphoroamidate, as described by: Moffatt, J. G.; Khorana, H. G. J. Am. Chem. Soc. 1961, 83, 649-58 and Moffatt, J. G. Can. J. Chem. 1964, 42, 599-604 and van Boom, J. H.; Crea, R.; Luyten, W. C.; Vink, A. B. Tetrahedron Lett. 1975, 16, 2779-82, or N-imidazole phosphoroamidate, as presented by Hoard, D. E.; Ott, D. G. J. Am. Chem. Soc. 1965, 87, 1785-8 and Shimazu, M.; Shinozuka, K.; Sawai, H. Tetrahedron Lett. 1990, 31, 235-8, with pyrophosphate. However, the reaction used in this method has many stages and lasts even a few days.

In one other method developed by Borch et al. and described in literature, the synthesis of nucleotide triphosphates involves generating a highly active intermediate product, i.e. pyrrolidine phosphoroamidate in the form of a dual ion, which undergoes fast condensation with tris(tetra-n-butylamine) pyrophosphate, as observed by Wu W.; Freel Meyers C. L.; Borch R. F. Org. Lett. 2004, 6, 2257-2260. Even though the authors ensure that the synthesis is highly efficient, it involves many laborious stages, which significantly lengthens the process of achieving the desired nucleotide triphosphates. The usefulness of these methods is limited due to the low efficiency of the synthesis, use of aggressive and expensive reagents, length of the reaction and bi-products contaminating the target triphosphate analogue.

The aim of the invention was the development of a new method of the synthesis of organic polyphosphate analogues, including in particular organic nucleoside polyphosphates, oligonucleotides, peptide carbohydrates or amino radicals, which is simpler, less costly and does not result in the production of by-products.

The aim of the invention is a method of synthesis of organic polyphosphates of general formula 1,

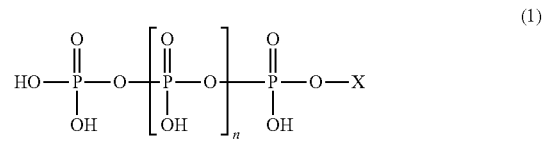

where n has a value of 0 to 2 while X stands for an organic radical, in particular nucleoside, oligonucleotide, peptide-carbohydrate or a protein radical is characterised in that it reacts with a compound of general formula 2,

OH—X  (2)

where X stands for the above while an adequate substituted derivative of 2-pyridyl-[1,3,2]oxazaphospholidine or an adequate substituted derivative of 2-pyrimidyl-[1,3,2]oxazaphospholidine of general formula 3

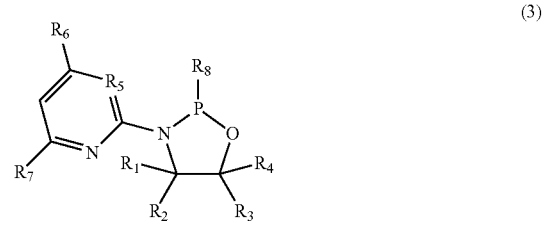

in which
R1, R2, R3, R4 are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent where saturated alkyl, unsaturated alkyl and aryl are partially or fully substituted,
$R_5$ stands for CH or N,
$R_6$ and $R_7$ stand for H or $CH_3$, halogen atom, $NO_2$, $NH_2$, $C_2H_5$
$R_8$ stands for a halogen atom or $NR_9R_{10}$, where $R_9$ and $R_{10}$ are the same or different and stand for ethyl, n-propyl, di-isopropyl,
and where $R_8$ stands for $NR_9R_{10}$, with $R_9$ and $R_{10}$ having the above-mentioned meaning, the amine is activated using weak acid, including especially 1-H-tetrazole or 5-ethylotio-1H-tetrazole.

Then the product of this reaction of general formula 4,

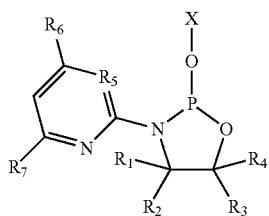
(4)

where $R_1$, $R_2$, $R_3$, $R_4$, $R_5$, $R_6$, $R_7$ and X stand for the above, is used in reaction with polyphosphoric acid ammonium salt of general formula 5 or 6

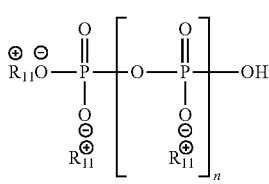
(5)

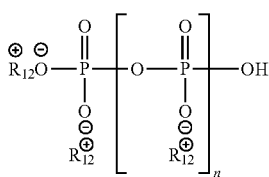
(6)

where n has a value of 0 to 2 while $R_{11}$ and $R_{12}$ stand for H or correspondingly at least one substituent $R_{11}$ stands for a group of general formula 7 while $R_{12}$ stands for a group of general formula 8,

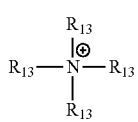
(7)

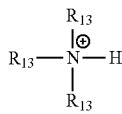
(8)

where substituent $R_{13}$ stands for $CH_3$ or $CH_2$—$R_{14}$ groups, where $R_{14}$ are the same or different and stand for a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl substituent where saturated alkyl, unsaturated alkyl and aryl are partially or fully substituted, and in the end of the reaction, the product is oxidized with iodine, preferably dissolved in pyridine, after which a compound of general formula 1 is isolated with well-known methods.

The method described in the invention preferably uses the monohydric polyphosphoric acid ammonium salt of general formula of 5 or 6, in which the $R_{11}$ or $R_{12}$ substituents stand for groups of general formula 7 or 8.

Moreover, the method preferably uses at least a double excess of the monohydric polyphosphoric acid ammonium salt.

The reactions used in the method should take place in organic solvents, preferably in acetonitrile or methylene chloride.

The second aspect of the invention is a development of a method of the synthesis of organic polyphosphates of the general formula 1,

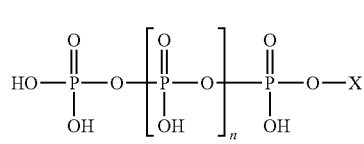
(1)

where n and X have the above-mentioned meaning, based on a reaction between the compound of general formula 4,

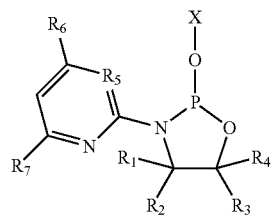
(4)

in which $R_1$, $R_2$, $R_3$, $R_4$, $R_5$, $R_6$, $R_7$ and X have the above-mentioned meaning, and the polyphosphoric acid ammonium salt of general formula 5 or 6,

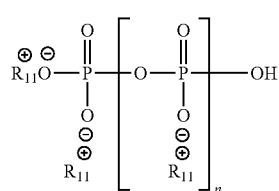
(5)

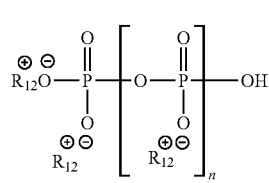
(6)

in which n has a value of 0 to 2, and $R_{11}$ and $R_{12}$ stand for H, or respectively at least one $R_{11}$ substituent stands for a group of general formula 7, while $R_{12}$ stands for a group of general formula 8, where the $R_{13}$ substituents stand for $CH_3$ or $CH_2$—$R_{14}$ groups, where $R_{14}$ are the same or different and stand for a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl substituent, where saturated alkyl, unsaturated alkyl and aryl are partially or fully substituted, and in the end of the reaction, the product is oxidized with iodine, preferably dissolved in pyridine, after which a compound of general formula 1 is isolated with well-known methods.

The method described by the invention preferably uses the monohydric polyphosphoric acid ammonium salt of general formula of 5 or 6, in which all the $R_9$ or $R_{10}$ substituents stand for a group of general formula 7 or 8.

Moreover, the method preferably uses at least double excess of polyphosphoric acid ammonium salt.

The reactions used in the method should take place in organic solvents, preferably in acetonitrile or methylene chloride.

The third aspect of the invention is the method of synthesis of organic polyphosphates of general formula 1

(1)

where n has a value of 0 to 2 while X stands for an organic radical, in particular nucleoside, oligonucleotide, peptide-carbohydrate or a protein radical characterised in that it enters into a reaction between a compound of general formula 2

OH—X    (2)

where X stands for the above, and an adequate substituted derivative of 3-(pyridine-2-yl)-[1,3,2]oxazaphospholidine or an adequate substituted derivative of 3-(pyrimidyl-2-yl)-[1,3,2]oxazaphospholidine of general formula 3

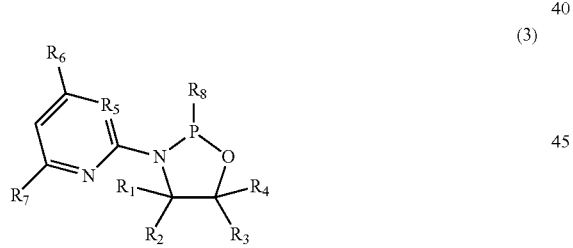
(3)

where
$R_1$, $R_2$, $R_3$, $R_4$ are the same or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent where saturated alkyl, unsaturated alkyl and aryl are partially or fully substituted, $R_5$ stands for CH or N, $R_6$ and $R_7$ stand for H or $CH_3$, halogen atom, $NO_2$, $NH_2$, $C_2H_5$ $R_8$ stands for a halogen atom or $NR_9R_{10}$ where $R_9$ i $R_{10}$ are the same or different and stand for ethyl, n-propyl, diisopropyl, However, when $R_8$ stands for $NR_9R_{10}$ where $R_9$ i $R_{10}$ stand for the above, the amine is activated using weak acid, including especially 1-H-tetrazole or 5-ethylotio-1H-tetrazole.

Then the product of this reaction of general formula 4,

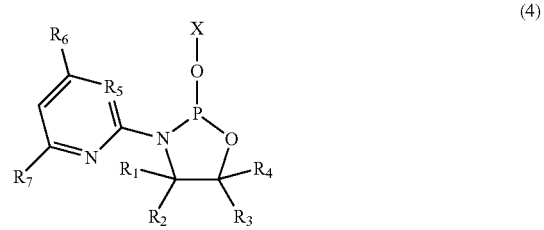
(4)

where $R_1$, $R_2$, $R_3$, $R_4$, $R_5$, $R_6$, $R_7$ and X stand for the above, is oxidized with iodine, preferably dissolved in pyridine, and an oxide of an adequate substituted derivative of 3-(pyridine-2-yl)-[1,3,2]oxazaphospholidine or an adequate substituted derivative of 3-(pyrimidyl-2-yl)-[1,3,2]oxazaphospholidine of general formula 9 is formed,

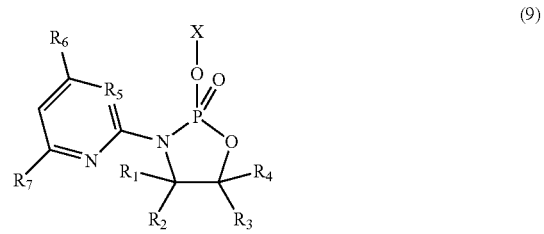
(9)

which, in turn, reacts with polyphosphoric acid ammonium salt of general formula 5 or 6

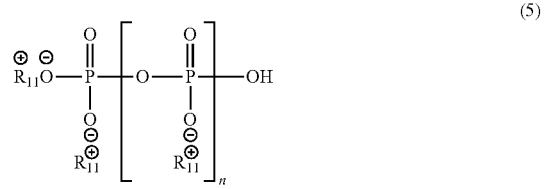
(5)

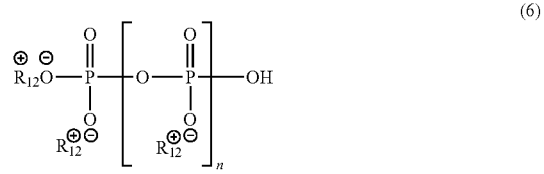
(6)

where n has a value of 0 to 2 while $R_{11}$ and $R_{12}$ stand for H or correspondingly at least one substituent $R_{11}$ stands for a group of general formula 7 while $R_{12}$ stands for a group of general formula 8, where substituents $R_{13}$ stand for $CH_3$ or $CH_2$—$R_{14}$ groups, where $R_{14}$ are the same or different and stand for a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl substituent, where saturated alkyl, unsaturated alkyl and aryl are partially or fully substituted, after which a compound of general formula 1 is isolated with well-known methods.

The method preferably uses the monohydric polyphosphoric acid ammonium salt of general formula of 5 or 6, in which all the $R_{11}$ or $R_{12}$ substituents stand for groups of general formula 7 or 8.

The method described by the invention preferably uses a double excess of the monohydric polyphosphoric acid ammonium salt.

The reactions should take place in organic solvents, preferably in acetonitrile.

The fourth aspect of the invention is a method of the synthesis of organic polyphosphates of general formula 1,

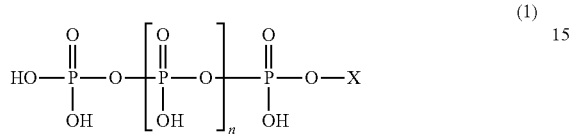
(1)

in which n and X have the above-mentioned meaning, based on a reaction of the compound of general formula 4,

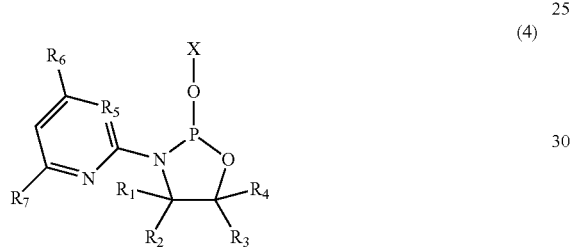
(4)

in which $R_1$, $R_2$, $R_3$, $R_4$, $R_5$, $R_6$, $R_7$ and X stand for the above, is oxidized with iodine, preferably dissolved in pyridine, and an oxide of an adequate substituted derivative of 3-(pyridine-2-yl)-[1,3,2]oxazaphospholidine or an adequate substituted derivative of 3-(pyrimidine-2-yl)-[1,3,2]oxazaphospholidine of general formula 9 is formed,

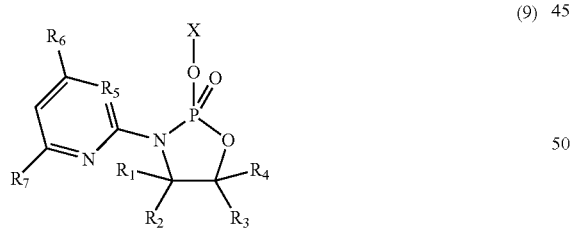
(9)

which, in turn, reacts with polyphosphoric acid ammonium salt of general formula 5 or 6,

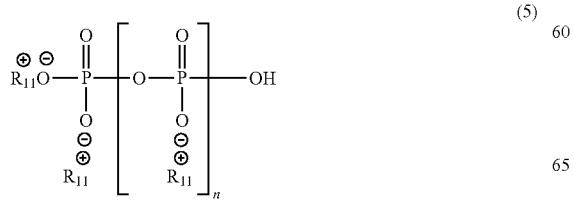
(5)

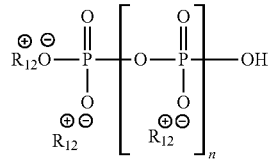
(6)

where n has a value of 0 to 2 while $R_{11}$ and $R_{12}$ stand for H or correspondingly at least one substituent $R_{11}$ stands for a group of general formula 7 while $R_{12}$ stands for a group of general formula 8, where the $R_{13}$ substituents stand for $CH_3$ or $CH_2$—$R_{11}$ groups, in which $R_{11}$ are the same or different and stand for a saturated alkyl with a chain of 1 to 8 carbon atoms, unsaturated alkyl with a chain of 1 to 8 carbon atoms, monocyclic aryl, saturated alkyl with a chain of 1 to 8 carbons and with a monocyclic or dicyclic aryl substituent, unsaturated alkyl with a chain containing 1 to 8 carbon atoms and with a monocyclic or dicyclic aryl substituent, in which the saturated alkyl, unsaturated alkyl and aryl are partly of fully substituted. After the end of the reaction the compound of general formula 1 is isolated using well-known methods.

The method preferably uses the monohydric polyphosphoric acid ammonium salt, in which all the $R_{11}$ substituents stand for groups of general formula 7 or $R_{12}$ stand for a group of general formula 8.

The method preferably uses at least a double excess of the polyphosphoric acid ammonium salt.

The reactions should take place in organic solvents, preferably in acetonitrile or methylene chloride.

The fifth aspect of the invention is a method of the synthesis of organic polyphosphates of general formula 1,

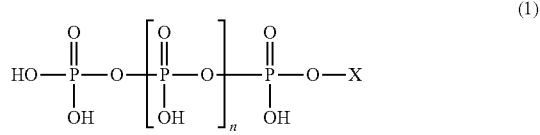
(1)

in which n and X have the above-mentioned meaning, based on a reaction of the compound of general formula 4,

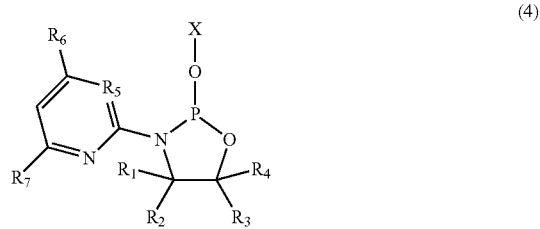
(4)

in which $R_1$, $R_2$, $R_3$, $R_4$, $R_5$, $R_6$, $R_7$ and X have the above-mentioned meaning, and the polyphosphoric acid ammonium salt

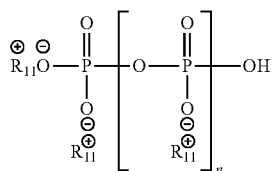
(5)

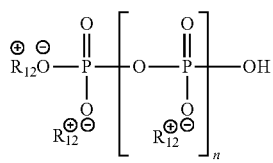
(6)

where n, $R_{11}$ and $R_{12}$ have the above meaning, in the presence of iodine, preferably dissolved in pyridine. The following reactions take place in the reaction mixture:
reaction between the compound of general formula 4 and the polyphosphoric acid ammonium salt,
oxidation of the compound of general formula 4 using iodine to an oxide of an adequate substituted derivative of 3-(pyridine-2-yl)-[1,3,2]oxazaphospholidine or an adequately substituted derivative 3-(pyrimidyl-2-yl)-[1,3,2]oxazaphospholidine,
reaction between the oxide of an adequate substituted derivative of 3-(pyridine-2-yl)-[1,3,2]oxazaphospholidine or an adequately substituted derivative 3-(pyrimidyl-2-yl)-[1,3,2]oxazaphospholidine and polyphosphoric acid ammonium salt.

After the end of the reaction, the compound of general formula 1 is isolated using well-known methods.

The method described in the invention preferably uses the monohydric polyphosphoric acid ammonium salt of general formula of 5 or 6, in which all the $R_{10}$ or $R_{11}$ substituents stand for groups of general formula 7 or 8.

The method preferably uses at least a double excess of the monohydric polyphosphoric acid ammonium salt and iodine, preferably dissolved in pyridine.

The reactions should take place in organic solvents, preferably in acetonitrile or methylene chloride.

The sixth aspect of the invention is a method employing solid bases, e.g. controlled pore glass CPG), which have hydroxyl groups. Hydroxyl groups of the bases are used to increase the nucleic acid (oligonucleotide) chain. The base is placed in reaction columns ensuring the flow of the liquid and gas.

The method of the synthesis of organic phosphates 1,

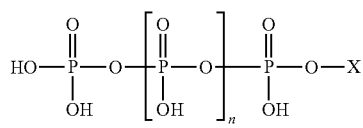
(1)

in which n has a value of 1 to 2, and X stands for the oligonucleotide or nucleic acid radical, is based on a reaction between a compound of general formula 2

X—OH (2)

in which X stands for the oligonucleotide or nucleic acid radical, and the compound of general formula 3,

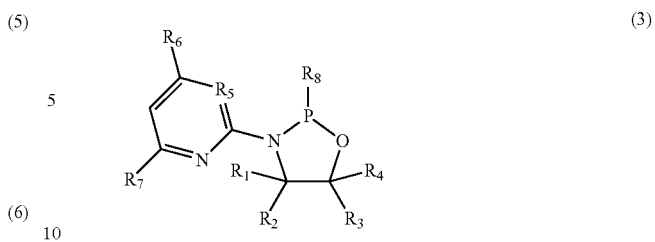
(3)

in which $R_1$, $R_2$, $R_3$, $R_4$, $R_5$, $R_6$, $R_7$ and $R_8$ have the above meaning, in the presence of weak acid, preferably monohydric with iodine in the presence of pyridine, including especially 1-H-tetrazole, 5-ethylotio-1H-tetrazole, 4,5-dicyanoimidazole, 5-benzylotio-1H-tetrazole, acetic acid. After the reaction has taken place and the excess of the solvents has been removed, and after the columns have been washed with dry acetonitrile, a mixture of the polyphosphoric acid ammonium salt of general formula 5 or 6, in which $R_{11}$ and $R_{12}$ have the above meanings, is applied to the column, with at least 20-50 times the stoichiometric excess of the mixture of the acid and iodine with respect to the available hydroxyl groups that are formed as a result of the increase of the nucleic acid chain on the surface of the solid phase. The reaction lasts from 5 to 25 minutes.

After the reaction has taken place, the product of the reaction is isolated using well-known methods.

The method described in the invention uses a mixture of the polyphosphoric acid ammonium salt, preferably monohydric, with iodine at the ratio of 1:0.8 to 0.8:1, preferably 1:1.

Compounds of general formula 5 and 6, in which n, $R_{11}$ and $R_{12}$ have the above meaning, preferably where all $R_{11}$ stand for a group of general formula 7 and $R_{12}$ stand for a group of general formula 8, are used as the polyphosphoric acid ammonium salt, preferably monohydric.

The method described in the sixth aspect of the invention is of great importance to chemical oligonucleotide syntheses on a solid phase using automatic nucleic acid synthesizer.

One advantage of the solution described in the invention is a simplified polyphosphate synthesis method, including especially that of nucleoside, oligonucleotide or carbohydrate polyphosphorates.

The method described in the invention is characterised by a shorter time of the process and simplified procedures necessary to produce the triphosphate analogue.

The invention may be used to produce triphosphate analogues of many compounds of biological importance, such as nucleosides, oligonucleotides, carbohydrates, peptides or proteins, which are a subject of comprehensive studies and development research due to their application potential in studies in the area of organic chemistry, molecular biology and biotechnology.

The invention can be illustrated by the following examples.

EXAMPLE 1

2-isopropyl-3-(pyrid-2-yl)-[1,3,2]oxazaphospholidine 50 mL of anhydrous benzene was placed in a flask under argon. The flask was then closed tightly, followed by an addition of a freshly distilled phosphoric chloride (III) (876λ 1; 10 mmole). The flask was then cooled down to a temperature of 5° C., and the anhydrous N,N-diisopropylamine (7.7 ml; 55 mmole) was added. The reaction mixture was stirred for 30 minutes, and then slowly heated to 25° C. The temperature was then maintained until the bis(N,N-diisopropylamine) chlorophosphite was formed. After the reaction was completed in 98% (about 3 days), 2-(2-pyridyl)aminoethanol (1.38 mg; 10 mmole) was added to entire content of the flask. Then, after about 2 hours, 1-H-tetrazole (700 mg; 10 mmole) dissolved in anhydrous benzene (5 mL) was added. After the entire content of the flask reacted, 1 µl of diisopropylamine was added. The product of the reaction was then eluted on the column filled with silica gel with 200-mesh molecules. The eluent phase used a mixture of solvents: benzene and triethylamine, with a benzene volume fraction of 90%. As a result of the reaction, 2-isopropyl-3-(pyrid-2-yl)-[1,3,2]oxazaphospholidine was obtained.

The efficiency of the reaction was 70%. The obtained product was lyophilized from the anhydrous benzene.

The produced compound was then analysed using nuclear magnetic resonance.

$^1$H NMR (400 MHz, DMSO-d$_6$)
λ 8.12 (dd, J=0.6, 4.85 Hz, 1H); 7.55 (dd, J=1.94, 7.24 Hz, 1H); 6.76 (dd, J=0.6, 8.4 Hz, 1H); 6.71 (dd, J=0.6, 4.85 Hz, 1H); 4.22 (m, 2H); 3.78 (m, 1H); 3.43 (m, 2H); 3.36 (m, 1H); 1.29 (m, 6H); 1.06 (m, 6H).

$^{13}$C NMR (100 MHz, DMSO-d$_6$) λ 156.4, 153.4, 148.3, 137.5, 116.2, 110.2, 109.1, 66.3, 62.1, 25.2, 23.6, 22.5, 22.4.

$^{31}$P NMR (121 MHz, DMSO) λ 115.3

EXAMPLE 2

Synthesis to -5'-O-[3-(pyridine-2-yl)-[1,3,2]oxazaphospholidin-2-yl]thymidine

3'-O-acetyl thymidyne (50 mg; 1.1 mmole) dissolved in anhydrous acetonitrile was placed in the flask under argon (10 mL). The flask was then closed tightly, followed by an addition of 1-H-tetrazole (180 mg; 1.8 mmole) and the 2-isopropyl-3-(pyrid-2-yl)-[1,3,2]oxazaphospholidine (260 mg; 1 mmole) obtained in accordance with example 1. The reaction mixture was then stirred for about two hours at room temperature until the reagents reacted. After the end of the reaction, the solvent was vaporized, and the product of the reaction was eluted on the column filled with silica gel with 200-mesh molecules. The eluent phase used a mixture of solvents: benzene and triethylamine, with triethylamine volume fracture of 10%. Then the collected fractions containing the product of the reaction, i.e. 5'-[3-(pyrid-2-yl)-[1,3,2]oxazaphospholidine]-3'-O-acetyl thymidyne were concentrated and lyophilised from anhydrous benzene. As a result of the reaction, 5'-O-[3-(pyrid-2-yl)-[1,3,2]oxazaphospholidine]-3'-O-acetyl thymidyne was obtained.

The efficiency of the reaction was at 70%. The achieved product had a form of a white solid, which was analysed by means spectroscopy.

$^1$H NMR (400 MHz, CDCl$_3$) δ (ppm) 8.9 (d, J=4.95 Hz, 1H); 7.62-7.58 (m, 2H); 7.34 (s, 1H); 6.80-6.77 (m, 1H); 6.20-6.19 (m, 1H); 5.30-5.28 (m, 1H); 4.57-4.48 (m, 2H); 4.14-4.07 (m, 1H); 4.01-3.97 (m, 1H); 3.59-3.52 (m, 2H); 3.47-3.39 (m, 1H); 2.29-2.26 (m, 1H); 2.20-2.18 (m, 1H); 2.01 (s, 3H); 1.78 (d, J=1.12 Hz, 3H)

$^{13}$C NMR (75 MHz, CD$_3$CN) λ (ppm) 170.6; 163.0; 156.2; 150.6; 138.3; 128.2; 115.4; 110.4; 107.6; 84.3; 83.6; 74.8; 69.3; 63.8; 45.8; 43.5; 36.9; 20.2; 11.6

$^{31}$P NMR (121 MHz, DMSO) λ (ppm) 131.47; 126.17

EXAMPLE 3

5'-triphosphorate-3'-O-acetyl thimidine

Synthesis in accordance with example 2, as a result of which 5'-O-[3-(pyrid-2-yl)-[1,3,2]oxazaphospholidine]-3'-O-acetyl thymidine was obtained serves as a basis for obtaining 5'-triphosphorate-3'-O-acetyl thimidine.

The 5'-O-[3-(pyrid-2-yl)-[1,3,2]oxazaphospholidine]-3'-O-acetyl thymidine (45 mg, 0.1 mM, 1 eq.) of general formula 7, obtained in accordance with example 2 and dissolved in anhydrous acetonitrile, was placed in the flask, followed by an addition of pyrophosphate tri(tetra-n-butylamine) (135.35 mg, 0.15 mM, 1.5 eq). The reaction mixture was then stirred for about two hours at room temperature until the cyclic intermediate product was produced ($^{31}$P NMR). Then iodine was added to the mixture (38 mg, 0.15 mM, 1.5 eq) dissolved in pyridine (0.5 mL) at a water volume fracture of 10% (v/v). After about 3 minutes the 3'-O-acetyl thymidine-5'ylo triphosphate was obtained.

The excess of iodine was resolved with ethanotiol, and the solvents were vaporised. The rest was then dissolved in water and washed twice with 10 ml of methylene chloride. Then the water was vaporised. The product of the reaction was isolated in a column filled with silica gel using a gradient of water in the mixture of 2-propanol and triethylamine with the volume fracture of triethylamine of 3%.

The fractions with the clean product were vaporised and lyophilised from dioxane. As the result of the reaction, 5'-triphosphorate-3'-O-acetyl thimidine was obtained.

The efficiency of the reaction was at 56%. The achieved product had a form of a white hygroscopic solid, which was analysed using spectroscopy.

$^1$H NMR (400 MHz, D$_2$O) δ (ppm) 7.81 (d, 1H); 6.41-6.36 (m, 1H); 4.74-4.69 (m, 1H); 4.3-4.23 (m, 2H); 4.09-4.0 (m, 1H); 3.236 (q, 6H); 2.43-2.38 (m, 2H); 1.96 (s, 3H); 1.35 (t, 9H).

$^{13}$C NMR (75 MHz, D$_2$O) λ (ppm) 166.55; 151.75; 137.42; 111.77; 85.65; 84.86; 65.58; 64.23; 46.63; 38.52; 11.61; 8.38.

$^{31}$P NMR (121 MHz, D$_2$O) λ (ppm) −8.8; −9.9; −22.6.

EXAMPLE 4

5'-triphosphorate-2',3'-O-diacetylouridine

Synthesis of 5'-O-[3-(pyrid-2-yl)-[1,3,2]oxazaphospholidine]-3'-O-acetyl uridine was according with procedure in example 2, however without purification and identification.

The crude of mixture containing 5'-O-[3-(pyridine-2-yl)-[1,3,2]oxazaphospholidine]-3'-O-acetyl uridine ((49.4 mg, 0.1 mM, 1 eq.), dissolved in anhydrous acetonitrile, was placed in the flask, followed by an addition of pyrophosphate tri(tetra-n-butylamine) (135.35 mg, 0.15 mM, 1.5 eq). The reaction mixture was then stirred for about two hours at room temperature until the cyclic intermediate product was produced ($^{31}$P NMR). Then iodine was added to the mixture (38 mg, 0.15 mM, 1.5 eq) dissolved in pyridine (0.5 mL) at a water volume fracture of 10% (v/v). After about 3 minutes the 3'-O-acetyl uridine-5'ylo triphosphate was obtained.

The excess of iodine was resolved with ethanotiol, and the solvents were vaporised. The rest was then dissolved in water and washed twice with 10 ml of methylene chloride. Then the water was vaporised. The product of the reaction was isolated in a column filled with silica gel using a gradient of water in the mixture of 2-propanol and triethylamine with the volume fracture of triethylamine of 3%.

The fractions with the clean product were vaporised and lyophilised from dioxane. As the result of the reaction, 5'-triphosphorate-3'-O-acetyl uridine was obtained.

The efficiency of the reaction was at 56%. The achieved product had a form of a white hygroscopic solid, which was analysed using spectroscopy.

$^1$H NMR (400 MHz, D$_2$O) δ (ppm) 11.04 (m, 1H); 7.58 (d, 1H); 6.38-6.32 (m, 1H); 5.54 (d, 1H); 5.21 (m, 1H); 4.65-4.61 (m, 1H); 4.3 (m, 2H); 4.09-4.0 (m, 1H); 1.36 (m, 6H)

$^{13}$C NMR (75 MHz, D$_2$O) λ (ppm) 178.23; 177.45; 159.22; 142.11; 128.23; 92.23; 87.23; 78.91; 66.59; 58.98; 57.35; 17.34; 16.76

$^{31}$P NMR (121 MHz, D$_2$O) λ (ppm) −9.3; −10.4; −22.9.

EXAMPLE 5

General Method of Cation Exchange in Polyphosphoric Acids on Ion Exchangers 2.23 g (5 mmole) of tetrasodium polyphosphate decahydrate was dissolved in 50 milliliters of double distilled water of a resistance of 18 miliohms. The solution was then passed through the column filled with DOWEX-50WX8 H$^+$ cation resin. The fraction was collected to a round-bottom flask with 2.78 g (15 mmole) of tributylamine dissolved in 20 ml of absolute ethanol and stirred using a magnetic stirrer in a temperature of 0° C. The column was washed with double distilled to achieve pH 7. The solution was then vaporised and lyophilised several times from water with dioxane until white powder, i.e. 2.5 g of tris(tri-n-butylamine)pyrophosphate, was produced (efficiency 69%).

EXAMPLE 6

Invention Used in the Synthesis of DNA and RNA Oligonucleotide 5'-Triphosphates on a Solid Phase In accordance with standard procedure, standard phosphoramidite series DNA i RNA was dissolved in acetonitrile at a concentration of 0.2 mmole and placed in a vessel filled with dry argon and connected to an automatic DNA synthesizer. The synthesis of oglinucleotides used the following synthetic blocks:
1. removal of the dimethoxytrityl group using 3% trichloroacetate in methylene chloride; duration 1.5 minutes
2. addition of an phosphoramidite unit in the presence of 0.05-mole solution tiotetrazole in acetonitrile
3. blocking of the unreacted hydroxyl groups using acetic anhydride in the presence of N-methylimidazole
4. oxidation of the phosphite bond with 0.5-mole solution of iodine in pyridine.

Four oligonucleotides, two in the DNA series and two in the RNA series, were synthesized in accordance with table 1. After the synthesis, the last dimethoxytrityl group was removed, and the cyclic phosphoramidite product of example 1 of formula:

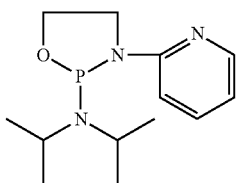 [SMILES: CC(C)N(C(C)C)P1OCCN1c1ccccn1]

was added to the reaction column in the presence of tioterea-zole solution. Condensation time: 12 minutes. After the reaction column had been washed, a solution of the pyrophosphate acid was added in the presence of a 0.5-mole iodine solution in the mixture of pyridine/acetonitrile. Duration: 30 minutes.

After the column had been washed, oligonucleotides were unlocked from the base using a nucleophilic reagent; data presented in table 1, column 2.

Oligonucleotides of the RNA series were subjected to the solution of tetrabutyl fluoride in tetrahydrofuran for 2 hours in order to remove protecting groups in 2', followed by a precipitation in methanol and elution using the high-performance liquid chromatography (HPLC)

Oligonucleotide triphosphate analogues were analysed using mass spectrometry, and the results were presented in table 1.

TABLE 1

| Oligonucleotide (typ) | The used method of deblocking the oligomer | Mass analysis | |
|---|---|---|---|
| | | The theoretical value | The observed value |
| PPP-TTTTTTTTTTTT (DNA) | conc. ammonia solution temp 25° C. time 30 min. | 3217.4 | 3219.5 |
| PPP-ATATATATATATA (DNA) | conc. ammonia solution temp 25° C. time 120 min. | 3262.45 | 3269.34 |
| PPP-UUUUUUUUUUUU (RNA) | AMA solution | 3237.19 | 3239.5 |
| PPP-GACUGACU (RNA) | AMA solution | 2747.27 | 2748.9 |

The invention claimed is:

1. A method of synthesis of organic polyphosphates of general formula 1:

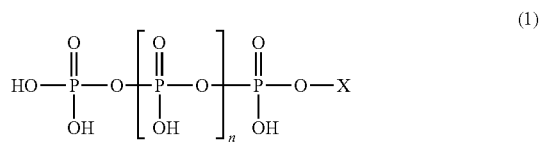

(1)

wherein n has a value of 0 to 2, and X is a nucleoside or an oligonucleotide, comprising:

(1) reacting a compound of general formula 2:

HO—X (2)

with a compound of general formula 3:

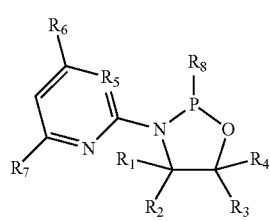

(3)

thereby forming a compound of general formula 4:

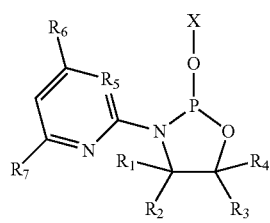

(4)

wherein
$R_1$, $R_2$, $R_3$, $R_4$ are identical or different and are H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent,
$R_5$ is CH or N,
$R_6$ and $R_7$ are H, $CH_3$, a halogen atom, $NO_2$, $NH_2$, or $C_2H_5$,
$R_8$ is halogen or $NR_9R_{10}$, wherein $R_9$ and $R_{10}$ are the same or different and are ethyl, n-propyl, or diisopropyl,
and wherein when $R_8$ is $NR_9R_{10}$, said reacting is carried out in the presence of a weak acid, (2) reacting the compound of general formula 4 with a polyphosphoric acid ammonium salt of general formula 5 or 6:

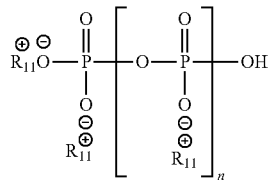

(5)

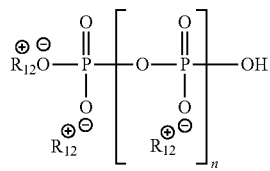

(6)

wherein n has a value of 0 to 2, $R_{11}$ and $R_{12}$ are H or correspondingly at least one $R_{11}$ is a group of general formula 7 and at least one of $R_{12}$ is a group of general formula 8:

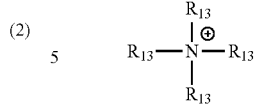

(7)

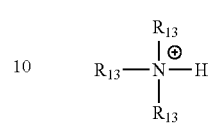

(8)

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, (3) oxidizing the product formed as a result of the reaction in (2) with iodine dissolved in pyridine, and (4) isolating the compound of general formula 1 from the product formed as a result of the oxidizing in (3).

2. A method of synthesis of organic polyphosphates of general formula 1:

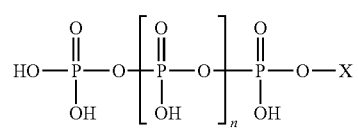

(1)

wherein n has a value of 0 to 2, and X is a nucleoside or an oligonucleotide, comprising:

(1) reacting a compound of general formula 4:

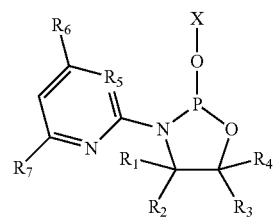

(4)

with a polyphosphoric acid ammonium salt of general formula 5 or 6:

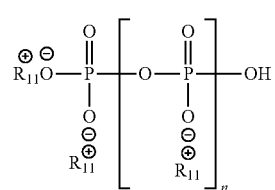

(5)

(6)

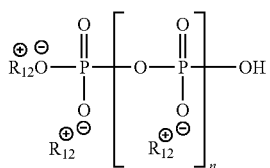

wherein $R_1$, $R_2$, $R_3$, $R_4$ are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent, $R_5$ is CH or N, $R_6$ and $R_7$ are H, $CH_3$, a halogen atom, $NO_2$, $NH_2$, or $C_2H_5$, n has a value of 0 to 2, $R_{11}$ and $R_{12}$ are H or correspondingly at least one $R_{11}$ is a group of general formula 7 and at least one of $R_{12}$ is a group of general formula 8:

(7)

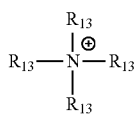

(8)

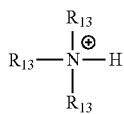

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, (2) oxidizing the product formed as a result of the reaction in (1) with iodine dissolved in pyridine, and (3) isolating the compound of general formula 1 from the product formed as a result of the oxidizing in (2).

3. A method of synthesis of organic polyphosphates of general formula 1:

(1)

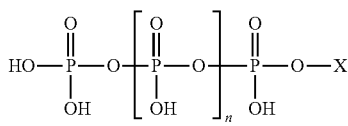

wherein n has a value of 0 to 2, and X is a nucleoside or an oligonucleotide, comprising:

(1) reacting a compound of general formula 2:

HO—X  (2)

with a compound of general formula 3:

(3)

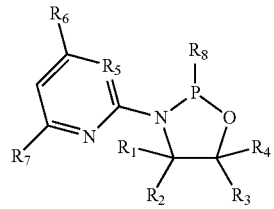

thereby forming a compound of general formula 4:

(4)

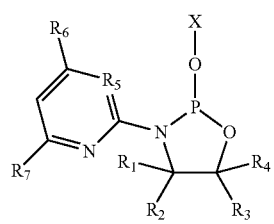

wherein $R_1$, $R_2$, $R_3$, $R_4$ are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent, $R_5$ is CH or N, $R_6$ and $R_7$ are H, $CH_3$, a halogen atom, $NO_2$, $NH_2$, or $C_2H_5$, $R_8$ is halogen or $NR_9R_{10}$, wherein $R_9$ and $R_{10}$ are the same or different and are ethyl, n-propyl, or diisopropyl, and wherein when $R_8$ is $NR_9R_{10}$, said reacting is carried out in the presence of a weak acid, (2) oxidizing the compound of general formula 4 with iodine dissolved in pyridine to form an oxide of general formula 9:

(9)

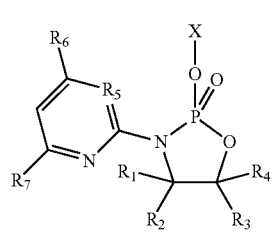

(3) reacting the compound of general formula 9 with a polyphosphoric acid ammonium salt of general formula 5 or 6:

(5)

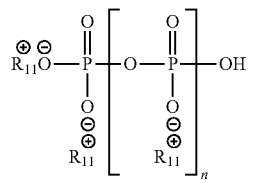

(6)

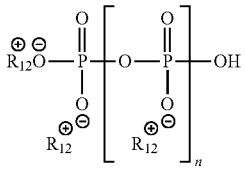

wherein n has a value of 0 to 2, $R_{11}$ and $R_{12}$ are H or correspondingly at least one $R_{11}$ is a group of general formula 7 and at least one of $R_{12}$ is a group of general formula 8:

(7)

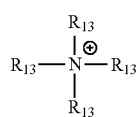

(8)

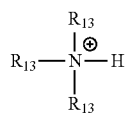

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, and (4) isolating the compound of general formula 1 from the product formed as a result of the reacting in (3).

4. A method of synthesis of organic polyphosphates of general formula 1:

(1)

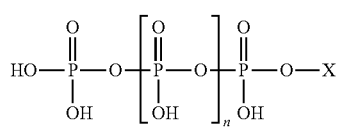

wherein n has a value of 0 to 2, and X is a nucleoside or an oligonucleotide, comprising:

(1) oxidizing a compound of general formula 4 with iodine dissolved in pyridine to form an oxide of general formula 9:

(4)

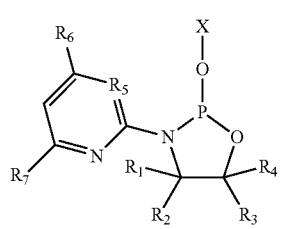

(9)

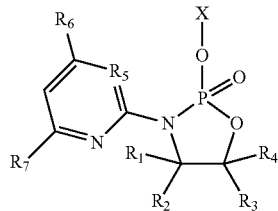

wherein
$R_1$, $R_2$, $R_3$, $R_4$ are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent,
$R_5$ is CH or N,
$R_6$ and $R_7$ are H, $CH_3$, a halogen atom, $NO_2$, $NH_2$, or $C_2H_5$,
(2) reacting the compound of general formula 9 with a polyphosphoric acid ammonium salt of general formula 5 or 6:

(5)

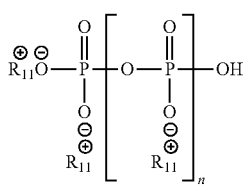

(6)

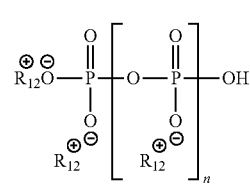

wherein n has a value of 0 to 2, $R_{11}$ and $R_{12}$ are H or correspondingly at least one $R_{11}$ is a group of general formula 7 and at least one of $R_{12}$ is a group of general formula 8:

(7)

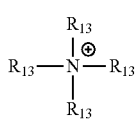

(8)

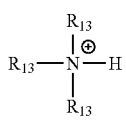

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, and (3) isolating the compound of general formula 1 from the product formed as a result of the reacting in (2).

5. A method of synthesis of organic polyphosphates of general formula 1:

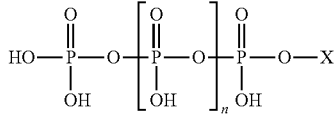 (1)

wherein n has a value of 0 to 2, and X is a nucleoside or an oligonucleotide, comprising:
(1) reacting a compound of general formula 4:

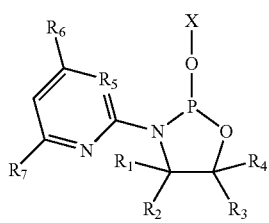 (4)

with a polyphosphoric acid ammonium salt of general formula 5 or 6:

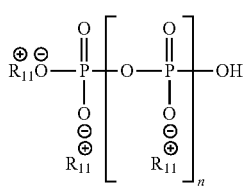 (5)

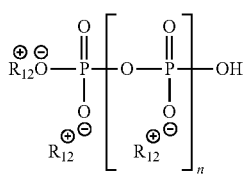 (6)

wherein
$R_1$, $R_2$, $R_3$, $R_4$ are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent,
$R_5$ is CH or N,
$R_6$ and $R_7$ are H, $CH_3$, a halogen atom, $NO_2$, $NH_2$, or $C_2H_5$,
n has a value of 0 to 2, $R_{11}$ and $R_{12}$ are H or correspondingly at least one $R_{11}$ is a group of general formula 7 and at least one of $R_{12}$ is a group of general formula 8:

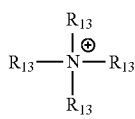 (7)

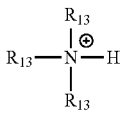 (8)

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, and when the reaction finishes,
(2) isolating the compound of general formula 1 from the product formed in (1) in the presence of iodine dissolved in pyridine.

6. A method of synthesis of organic polyphosphates of general formula 1:

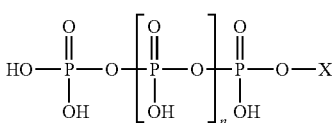 (1)

wherein n has a value of 0 to 2, and X is a nucleoside or an oligonucleotide, on a solid support, comprising:
(1) reacting in a column and in the presence of a solvent, a compound of general formula 2:

 (2)

with a compound of general formula 3:

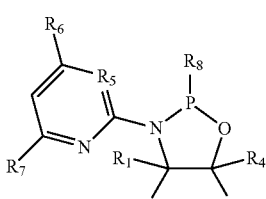 (3)

wherein
$R_1$, $R_2$, $R_3$, $R_4$ are identical or different and stand for H or a saturated alkyl with a chain of 1 to 8 carbons, unsaturated alkyl with a chain of 1 to 8 carbons, a monocyclic aryl, unsaturated alkyl with a chain of 1 to 8 carbons containing a monocyclic or bicyclic aryl substituent,
$R_5$ is CH or N,
$R_6$ and $R_7$ are H, $CH_3$, a halogen atom, $NO_2$, $NH_2$, or $C_2H_5$,
$R_8$ is halogen or $NR_9R_{10}$, wherein $R_9$ and $R_{10}$ are the same or different and are ethyl, n-propyl, or diisopropyl,
and wherein when $R_8$ is $NR_9R_{10}$, said reacting is carried out in the presence of a weak acid,
(2) after the reaction finishes, removing excess solvent and washing the column with dry acetonitrile,
(3) applying to the column a polyphosphoric acid ammonium salt of general formula 5 or 6:

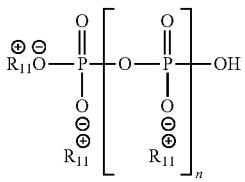

(5)

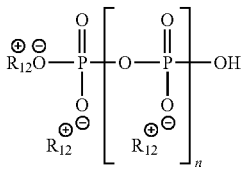

(6)

wherein n has a value of 0 to 2, $R_{11}$ and $R_{12}$ are H or correspondingly at least one $R_{11}$ is a group of general formula 7 and at least one of $R_{12}$ is a group of general formula 8:

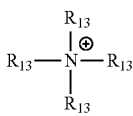

(7)

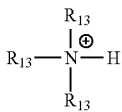

(8)

wherein $R_{13}$ is $CH_3$ or $CH_2$—$R_{14}$ groups, wherein $R_{14}$ is the same or different and is a saturated alkyl with a chain of 1 to 8 carbons, unsaturated alkyl with a chain of 1 to 8 carbons, a monocyclic aryl, saturated alkyl with a chain of 1 to 8 carbons containing a monocyclic or bicyclic aryl substituent, unsaturated alkyl with a chain of 1 to 8 carbons containing a monocyclic or bicyclic aryl, and iodine in the presence of pyridine, and reacting the polyphosphoric acid ammonium salt with the iodine, wherein at least 20 times stoichiometric excess of acid and iodine mixture is used in relation to the available hydroxyl groups created in the process of a growth of nucleic acid chain on the surface of a solid phase, and when the reaction finishes (3) isolating the compound of general formula 1 from the product formed in (2).

7. The method according to claim 1 wherein monohydric polyphosphoric acid ammonium salt of general formula 5 or 6 is used, where substituents $R_{11}$ or $R_{12}$ are groups with formulas 7 or 8.

8. The method according to claim 1 wherein at least a double stoichiometric excess of polyphosphoric acid ammonium salt relative to the compound of formula 4 is used.

9. The method according to claim 1 wherein $R_8$ is $NR_9R_{10}$ and the weak acid is 1-H-tetrazole or 5-ethylthio-1H-tetrazole.

10. The method according to claim 2 wherein monohydric polyphosphoric acid ammonium salt of general formula 5 or 6 is used, where substituents $R_{11}$ or $R_{12}$ are groups with formulas 7 or 8.

11. The method according to claim 2 wherein at least a double stoichiometric excess of polyphosphoric acid ammonium salt relative to the compound of formula 4 is used.

12. The method according to claim 3 wherein monohydric polyphosphoric acid ammonium salt of general formula 5 or 6 is used, where substituents $R_{11}$ or $R_{12}$ are groups with formulas 7 or 8.

13. The method according to claim 3 wherein at least a double stoichiometric excess of polyphosphoric acid ammonium salt relative to the compound of formula 4 is used.

14. The method according to claim 3 wherein $R_8$ is $NR_9R_{10}$ and the weak acid is 1-H-tetrazole or 5-ethylthio-1H-tetrazole.

15. The method according to claim 4 wherein monohydric polyphosphoric acid ammonium salt of general formula 5 or 6 is used, where substituents $R_{11}$ or $R_{12}$ are groups with formulas 7 or 8.

16. The method according to claim 4 wherein at least a double stoichiometric excess of polyphosphoric acid ammonium salt relative to the compound of formula 4 is used.

17. The method according to claim 5 wherein monohydric polyphosphoric acid ammonium salt of general formula 5 or 6 is used, where substituents $R_{11}$ or $R_{12}$ are groups with formulas 7 or 8.

18. The method according to claim 5 wherein at least a double stoichiometric excess of polyphosphoric acid ammonium salt relative to the compound of formula 4 is used.

19. The method according to claim 6 wherein monohydric polyphosphoric acid ammonium salt of general formula 5 or 6 is used, where substituents $R_{11}$ or $R_{12}$ are groups with formulas 7 or 8.

20. The method according to claim 6 wherein a mixture of polyphosphoric acid ammonium salt and iodine is used in the ratio of 1:0.8 to 0.8:1.

21. The method according to claim 6 wherein at least 50 times stoichiometric excess of acid and iodine mixture is used.

22. The method according to claim 6 wherein $R_8$ is $NR_9R_{10}$ and the weak acid is 1-H-tetrazole or 5-ethylthio-1H-tetrazole.

* * * * *